United States Patent [19]

Liberman

[11] Patent Number: 4,840,034
[45] Date of Patent: Jun. 20, 1989

[54] METHOD OF FREEZING VITAL BODY FLUIDS

[75] Inventor: Barnet L. Liberman, 421 Hudson St., New York, N.Y. 10014

[73] Assignees: Barnet L. Liberman; Winthrop D. Chamberlain, both of New York; Joseph Fedele; Brian Fedele, both of Queens, all of N.Y. ; a part interest

[21] Appl. No.: 219,339

[22] Filed: Jul. 14, 1988

[51] Int. Cl.⁴ ............................................. F25D 17/02
[52] U.S. Cl. ........................................ 62/64; 62/78; 426/524; 435/1
[58] Field of Search ................ 62/64, 78; 435/1; 426/524

[56] References Cited

U.S. PATENT DOCUMENTS

| | | | |
|---|---|---|---|
| 4,059,967 | 11/1977 | Rowe et al. | 62/78 |
| 4,309,449 | 1/1982 | O'Roark et al. | 62/64 |
| 4,601,909 | 7/1986 | Nagoshi | 62/64 |
| 4,654,217 | 3/1987 | Nagoshi | 62/64 |
| 4,657,768 | 4/1987 | Nagoshi | 62/64 |
| 4,689,963 | 9/1987 | Sakai | 62/64 |

*Primary Examiner*—Ronald C. Capossela
*Attorney, Agent, or Firm*—Cohen, Pontani & Lieberman

[57] ABSTRACT

A method of freezing vital body fluids for storage and later use is provided. The method includes the steps of preparing a brine including a cruciferous oil, cooling the brine, providing a heat transfer container having a vital body fluid therein and subjecting the heat transfer container to a heat transfer relationship with the cooled brine for a period of time sufficient to freeze the vital body fluid in the heat transfer container.

20 Claims, 1 Drawing Sheet

METHOD OF FREEZING VITAL BODY FLUIDS

BACKGROUND OF THE INVENTION

This invention relates generally to methods of freezing vital body fluids and, in particular, to a method of freezing vital body fluids which prevents deterioration of the cellular structure of the components of the fluids s as to maintain their viability.

Methods of freezing vital body fluids such as sperm, eggs, zygotes, blood and the like for storage and later use are known. In particular, vital body fluids are often frozen using liquid nitrogen which is available at a temperature of 320.4° F. (−195.8° C.) The vital body fluids frozen by this method cannot be maintained at such a low temperature for an extended period of time as the cellular structure within the fluid deteriorates and viability of the fluids is not maintained.

A Method of Freezing Fishery Products is known from U.S. Pat. No. 4,601,909 issued to Nagoshi on July 22, 1986. The method of Nagoshi includes the steps of preparing a brine containing rapeseed oil, propylene glycol, calcium chloride and water, cooling the brine and immersing the seafood in the cooled brine until it is frozen. This method reduces or eliminates breakdown of muscle tissue and deterioration in quality of the seafood.

A similar process for Quick Freezing of Meat is disclosed and claimed in U.S. Pat. No. 4,654,217 issued to the same inventor on March 31, 1987. The process disclosed in this later patent is similar to that disclosed in the earlier patent except that it is applicable to beef, poultry, pork and the like.

U.S. Pat. No. 4,657,768 issued to Nagoshi on April 14, 1987, discloses a Freezing Method for Perishable Foods which includes placing a perishable food in a heat conducting container. The opposite surface of the heat conducting container is then placed into contract with a cooled brine or a liquified gas. The perishable food is frozen quickly without immersion of the food in the cooled brine.

Another method of freezing foods is disclosed in U.S. Pat. No. 4,689,963 issued to Skai on Sept. 1, 1987. The method of Sakai includes placement of a perishable food and a layer of brine into a heat conducting container. The opposite side of the heat conducting container is positioned in a heat transfer relationship with a cooled brine. Freezing proceeds through the perishable food from the portion that is in contact with the brine, and the potential for the food sticking to the container is reduced.

There is no teaching or suggestion in any of these patents that the processes disclosed can be used to freeze vital body fluids and maintain their viability over an extended period of time. Accordingly, it is desirable to provide a process for freezing vital body fluids such as sperm, eggs, zygotes, blood and the like which prevent deterioration in the cellular structure of the body fluid.

It is, therefore, an object of the invention to provide a process for quick freezing body fluids that maintains the viability of the fluid.

Another object of the invention is to provide a method of freezing body fluids by chilling the fluid using a brine including a cruciferous oil.

A further object of the invention is to provide a method of freezing body fluids which does not destroy the cellular structure of the fluid.

Still another object of the invention is to provide an economical method of freezing body fluids.

Still other objects and advantages of the invention will in part be obvious and will in part be apparent from the specification.

SUMMARY OF THE INVENTION

Generally speaking, in accordance with the invention, a method for freezing body fluids for extended storage is provided. The method includes the steps of preparing a brine including a suitable oil; cooling the brine to a temperature between about −22° and −43.6° F.; providing a heat transfer container including a vital body fluid therein; and subjecting the heat transfer container to a heat transfer relationship with the cooled brine for a period of time sufficient to freeze the vital body fluid contained in the heat transfer container. The brine generally includes a glycol, a salt and water in addition to the suitable oil.

The invention accordingly comprises the several steps and the relation of one or more of such steps with respect to each of the others thereof which will be exemplified in the method hereinafter disclosed and the scope of the invention will be indicated in the claims.

BRIEF DESCRIPTION OF THE DRAWINGS

For a fuller understanding of the invention, reference is had to the following description taken in connection with the accompanying drawings, in which.

DETAILED DESCRIPTION OF THE PREFERRED EMBODIMENTS

Figure 1:
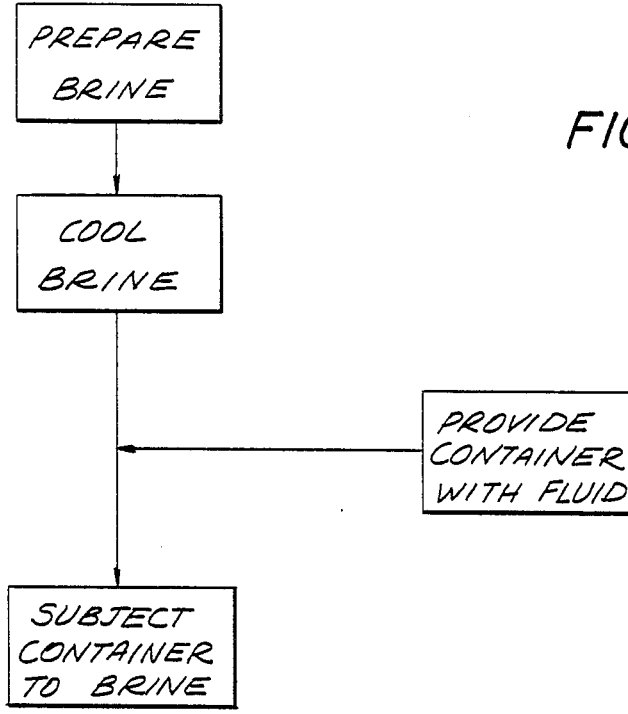
FIG. 1 is a flow diagram showing the method of the invention.

The first step of the process of freezing vital body fluids in accordance with the invention is preparation of a brine solution. The brine solution includes a suitable oil, generally a cruciferous oil. In a preferred embodiment, oil from a plant of the genus Brassica is used. These oils include, but are not limited to, oil of Brassica campestris, otherwise known as rapeseed oil, and oil of Brassica hirta, also known as mustard oil.

Rapeseed oil has a solidification point of 14° F. (−10° C. ), a specific gravity at 59° F. (15° C.) of 0.915, a refractive index at 122° F. (50° C.) of 1.4709, an iodine value of 98.6 and a saponification value of 174.7. The oil contains about 1% palmitic acid, about 32% oleic acid, about 15% linoleic acid, about 1% linolenic acid and about 50% erucic acid. The percentages expressed are percentages of total fatty acids in the oil.

The only saturated component of the oil is palmitic acid. Palmitic acid has 16 carbon atoms and a molecular weight of 256.4.

Oleic acid, also known as (Z)-9-octadecenoic acid, has 18 carbon atoms and a molecular weight of 282.5. The position of unsaturation is between the ninth and tenth carbon atoms in the chain. The molecule has a cis configuration.

Linoleic acid has two positions of unsaturation and is also known as cis,cis-9,12-octadecadienoic acid. The acid has 18 carbon atoms and a molecular weight of 280.5.

Linolenic acid has three positions of unsaturation and is also known as (Z,Z,Z)-9,12,15-octadecatrienoic acid. Linolenic acid has 18 carbon atoms and molecular weight of 278.4.

Erucic acid, a major component of the oils of the genus Brassica, is also known as (Z)-13-docosenoic acid. Erucic acid has 22 carbon atoms with one position of unsaturation and a molecular weight of 338.6.

Mustard oil is similar. Mustard oil has a specific gravity at 59° F. of 0.9145, a refractive index at 122° F. of 1.475, an iodine value of 102 and a saponification value of 174. Mustard oil includes about 1.3% by weight myristic acid, about 27.2% by weight oleic acid, about 16.6% by weight linoleic acid, about 1.8% by weight linolenic acid, about 1.1% by weight behenic acid, about 1.0% by weight lignoceric acid and about 51.0% by weight erucic acid.

In the case of mustard oil, the sole saturated component is myristic acid. Myristic acid has 14 carbon atoms and is also known as tetradecanoic acid. The molecular weight of myristic acid is 228.4.

Behenic acid has 22 carbon atoms and is also known as docosanoic acid. It has a molecular weight of 340.6.

Lignoceric acid has 24 carbon atoms and is also known as tetracosanoic acid. It has a molecular weight of 368.6. The other components of mustard oil are also present in rapeseed oil and are described above.

The oil is used in an amount less than about 1% by weight, more preferably less than about 0.8% by weight and most preferably between about 0.1 and 0.5% by weight of the brine.

It is to be understood that oils, especially cruciferous oils, other than rapeseed oil and mustard oil can be used in accordance with the invention. In addition, synthetic oils having the characteristics described would be useful. The manner in which the oils function is described in detail below and it will be readily apparent that other oils will function acceptably in accordance with the invention and can be readily determined.

In addition to the oil, the brine also generally includes a glycol, an inorganic salt and water. Suitable glycols include, but are not limited to, ethylene glycol, propylene glycol, benzylene glycol, butylene glycol, diethylene glycol, diphenyl glycol, ethylidene glycol, and the like. Any glycol can be used alone or in combination with other glycols. Propylene glycol is used in a preferred embodiment. The glycol component is present in an amount between about 30 and 50% by weight of the brine, more preferably between about 35 and 45% by weight and most preferably in an amount of about 40% by weight.

Salts which ar useful in accordance with the invention include, but are not limited to, calcium chloride, calcium bromide, calcium iodide, potassium chloride, potassium bromide, potassium iodide and the like. Calcium chloride is used in a preferred embodiment. The salt is present in an amount between about 5 and 15% by weight of the brine, more preferably in an amount between about 7 and 13% by weight and most preferably in an amount of about 10% by weight.

Water is present in an amount between about 40 and 60% by weight, more preferably in an amount between about 45 and 55% by weight and most preferably in an amount of about 50% by weight.

In an especially preferred embodiment, the brine has the following composition:

| Component | Amount (% by weight) |
| --- | --- |
| Cruciferous oil | 0.1–0.5 |
| Propylene glycol | 40 |
| Calcium chloride | 10 |
| Water | about 50 |

The cruciferous oil is preferably rapeseed oil or mustard oil.

The brine is cooled to a temperature between about −22° and −43.6° F. It is currently believed that as a result of such cooling fine ice crystals form in the brine and are uniformly distributed at these temperatures. Assuming this to be true, then it is believed that the ice crystals permit efficient cold transfer and an increase in the expected freezing rate of a vital body fluid placed into a heat transfer relationship with brine. Consequently, the time required to freeze the vital body fluid is reduced. In a preferred embodiment, means are provided for withdrawing heat from the brine s that the temperature of the brine remains substantially constant when a vital body fluid is placed into a heat transfer relationship therewith. It is presently believed that the vital body fluid passes rapidly through the zone of maximum ice crystal formation, that is, between about 23° and 31.1° F. (−5° and −0.5° C.) thereby preventing formation of ice crystals, breakdown of cellular tissue and deterioration of the vital body fluid is minimized.

The oil is believed to be the component of the brine which increases the freezing rate of the vital body fluid brought into a heat transfer relationship with the cooled brine. The cruciferous oil is, therefore, a significant component even though it is used in a relatively small amount.

Vital body fluids are collected by known techniques for freezing in accordance with the invention. Suitable body fluids which can be frozen for storage include, but are not limited to, sperm, eggs, zygotes, blood and the like. The collected body fluids are stored in suitable heat transfer containers such as plastic bag and the like. It is to be understood that the scope of the invention is not intended to be limited by the particular body fluid used or the heat transfer container in which the body fluid is stored.

The vital body fluid is frozen by placing the heat transfer container in which it is maintained into a heat transfer relationship with the cooled brine. The container can be placed into a heat transfer relationship by immersing the container in the cooled brine. Alternatively, the container may be placed in a heat transfer pan or tray and the heat transfer pan or tray can be placed into contact with the cooled brine. As another alternative for placing the heat transfer container having the vital body fluid therein into heat transfer relationship with the cooled brine, the container may be placed in a heat transfer pan or tray including a small amount of brine and the heat transfer pan or tray can be brought into a heat transfer relationship with the cooled brine. Although the precise amount of time necessary to freeze the vital body fluid is dependent on the amount of fluid and to a limited extent on the nature of the heat transfer container having the fluid therein, up to about one half pint of vital body fluid can often be frozen in a period of between about on-ehalf and 2 minutes.

Figure 2:
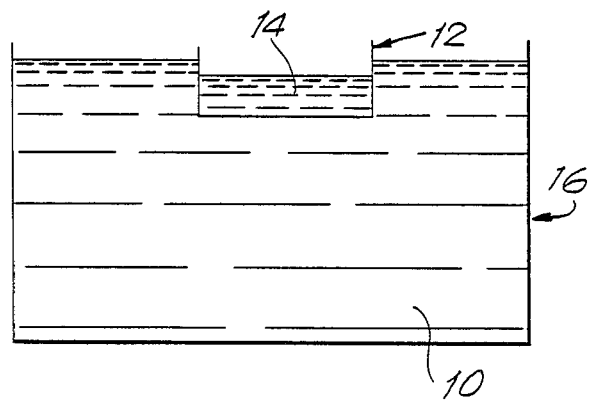
FIG. 2 is a cross-sectional plan view of an apparatus for use in performing the method of the invention.

FIG. 2 shows an apparatus for carrying out the method of the invention wherein a brine 10 is contained within a suitable container 16. A vital body fluid 14 is provided in a second container 12. Second container 12 is shown in contact with brine 10 so that the vital body fluid 14 in second container 12 can be frozen in accordance with the method of the invention.

Vital body fluids frozen by the method described do not deteriorate significantly and can be stored for an extended period of time. Upon thawing, which preferably should be performed on such a frozen fluid in a relatively rapid manner, the fluid can be used as if it had never been frozen. Additionally, freezing of body fluids, especially blood, is useful for inactivating cold sensitive viruses and other organisms contained in the fluid. Examples of cold sensitive viruses which would be inactivated using this method include the HIV virus, which causes AIDS and hepatitis viruses.

It will thus be seen that the objects set forth above, among those made apparent from the preceding description, are efficiently attained and, since certain changes may be made in carrying out the above method without departing from the spirit and scope of the invention, it is intended that all matter contained in the above description shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

Particularly, it is to be understood that in said claims, ingredients of compounds recited in the singular are intended to include compatible mixtures of such ingredients wherever the sense permits.

What is claimed is:

1. A method of freezing vital body fluids comprising:
   preparing a brine including at least 0.1% by weight of cruciferous oil;
   cooling the brine to a temperature between about $-22°$ and $-43.6°$ F.;
   providing a heat transfer container including a vital body fluid therein; and
   bringing the heat transfer container into a heat transfer relationship with the cooled brine for a period of time sufficient to transmit cold from the cooled brine to the vital body fluid in the heat transfer container and freeze the vital body fluid.

2. The method of freezing vital body fluids of claim 1, wherein the oil is extracted from a plant of the genus Brassica.

3. The method of freezing vital body fluids of claim 1, wherein the oil is selected from the group consisting of rapeseed oil, mustard oil and mixtures thereof.

4. The method of freezing vital body fluids of claim 1, wherein the oil contains erucic acid as the single largest component.

5. The method of freezing vital body fluids of claim 1, wherein the oil contains less than about 2% saturated components.

6. The method of freezing vital body fluids of claim 1, wherein the oil is used in an amount between about 0.1 and 0.5% by weight of the brine.

7. The method of freezing vital body fluids of claim 1, wherein the brine further includes a glycol, an inorganic salt and water.

8. The method of freezing vital body fluids of claim 7, wherein the glycol is propylene glycol.

9. The method of freezing vital body fluids of claim 7, wherein the glycol is present in an amount between about 30 and 50% by weight of the brine.

10. The method of freezing vital body fluids of claim 7, wherein the salt is calcium chloride.

11. The method of freezing vital body fluids of claim 7, wherein the salt is present in an amount between about 40 and 60% by weight of the brine.

12. The method of freezing vital body fluids of claim 7, wherein the water is present in an amount between about 40 and 60% by weight of the brine.

13. The method of freezing vital body fluids of claim 1, wherein the vital body fluid is selected from the group consisting of sperm, eggs, zygotes and blood.

14. The method of freezing vital body fluids of claim 1, wherein the vital body fluid is brought into a heat transfer relationship with the brine for a period between about $\frac{1}{2}$ and 2 minutes.

15. The method of freezing vital body fluids of claim 1, wherein the vital body fluid is brought into a heat transfer relationship by immersion of the heat transfer container having the vital body fluid therein in the cooled brine.

16. The method of freezing vital body fluids of claim 1, wherein the vital body fluid is brought into a heat transfer relationship with the cooled brine by placing the heat transfer container having the vital body fluid therein in a heat transfer pan and subjecting the heat transfer pan to the cooled brine.

17. The method of freezing vital body fluids of claim 1, wherein the vital body fluid is brought into a heat transfer relationship by placing the heat transfer container having the vital body fluid therein into a heat transfer tray along with sufficient brine to at east coat the bottom of the tray and subjecting the heat transfer tray to the cooled brine.

18. A method of freezing vital body fluids comprising:
    preparing a brine including an effective amount of a suitable oil for increasing the freezing rate of a vital body fluid brought into a heat transfer relationship therewith so as to minimize deterioration in the cellular structure of the body fluid;
    cooling the brine to a temperature between about $-22°$ and $-43.6°$ F.;
    providing a heat transfer container including a vital body fluid therein;
    bringing the heat transfer container into a heat transfer relationship with the cooled brine for a period of time sufficient to freeze the vital body fluid.

19. A method of freezing vital body fluids of claim 18, wherein the brine includes between about 0.1 and 1.0% by weight of an oil selected from the group consisting of rapeseed oil, mustard oil and mixtures thereof.

20. A method of freezing vital body fluids of claim 18, wherein the brine further includes about 30 and 50% by weight of a glycol, between about 5 and 15% by weight of salt and a balance of water.

* * * * *